(12) United States Patent
Soring et al.

(10) Patent No.: US 7,025,735 B2
(45) Date of Patent: Apr. 11, 2006

(54) ULTRASONIC APPARATUS FOR THE TREATMENT OF SEPTIC WOUNDS

(75) Inventors: Holger Soring, Quickborn (DE); Jorg Soring, Holm (DE)

(73) Assignee: Soring GmbH Medizintechnik, Quickborn (DE)

( * ) Notice: Subject to any disclaimer, the term of this patent is extended or adjusted under 35 U.S.C. 154(b) by 288 days.

(21) Appl. No.: 09/861,765

(22) Filed: May 21, 2001

(65) Prior Publication Data

US 2002/0062093 A1    May 23, 2002

(30) Foreign Application Priority Data

Nov. 20, 2000    (DE)    ............. 200 19 711 U

(51) Int. Cl.
*A61H 1/00*    (2006.01)

(52) U.S. Cl. ............... 601/2; 601/3; 601/4; 600/439; 600/459; 310/311; 310/322; 310/334; 310/340; 604/22

(58) Field of Classification Search ............. 601/2–4; 600/439, 459; 310/311, 322, 334, 340; 604/22
See application file for complete search history.

(56) References Cited

U.S. PATENT DOCUMENTS

| 3,645,255 | A |   | 2/1972  | Robinson |
|-----------|---|---|---------|----------|
| 4,982,730 | A | * | 1/1991  | Lewis, Jr. ................... 128/24 |
| 5,116,343 | A | * | 5/1992  | Ams et al. .................. 606/128 |
| 5,525,172 | A | * | 6/1996  | Cadiou ....................... 156/73.1 |
| 5,702,360 | A | * | 12/1997 | Dieras et al. ................. 604/22 |
| 5,707,636 | A | * | 1/1998  | Rodriguez et al. .......... 424/401 |
| 5,735,811 | A |   | 4/1998  | Brisken |
| 5,931,805 | A |   | 8/1999  | Brisken |
| 6,280,441 | B1 | * | 8/2001 | Ryan ............................ 606/45 |

\* cited by examiner

*Primary Examiner*—Shawntina Fuqua
(74) *Attorney, Agent, or Firm*—Horst M. Kasper

(57) ABSTRACT

An ultrasonic apparatus comprising a hand piece (1) within a handle region (2), a connection tube (3) for connecting to a supply tube, wherein rock salt solution and medical healing agents such as heparin, antibioticts and the like are fed through the feed channel (5) to the sonotrode (7) or ultrasonic treatment head. The ultrasound energy is fed to the hand piece (1) through the connection line to the ultrasonic generator (4) in a conventional way.

36 Claims, 3 Drawing Sheets

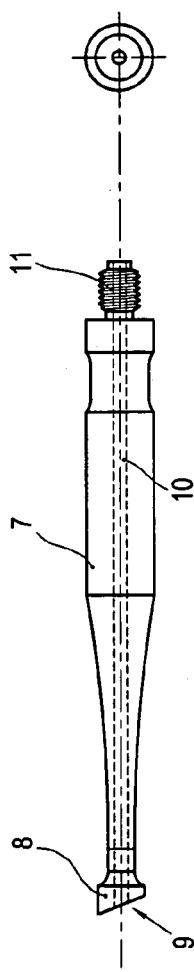
Fig.2a / Fig.2b
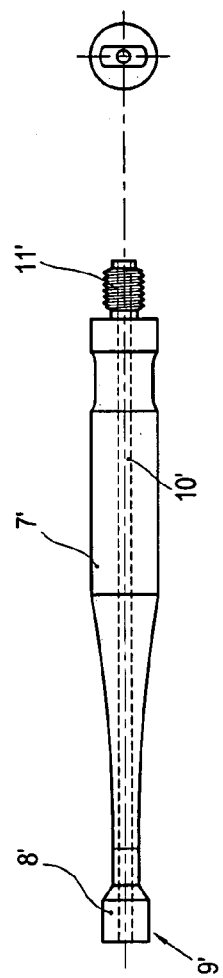
Fig.3a / Fig.3b
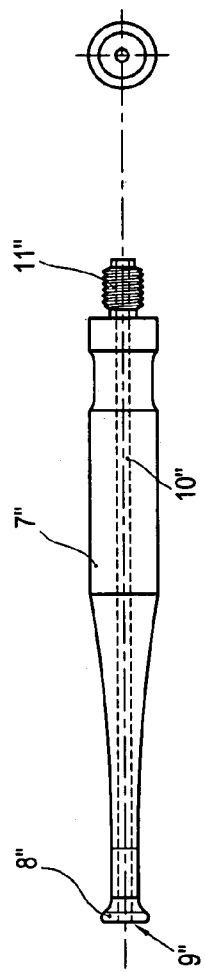
Fig.4a / Fig.4b
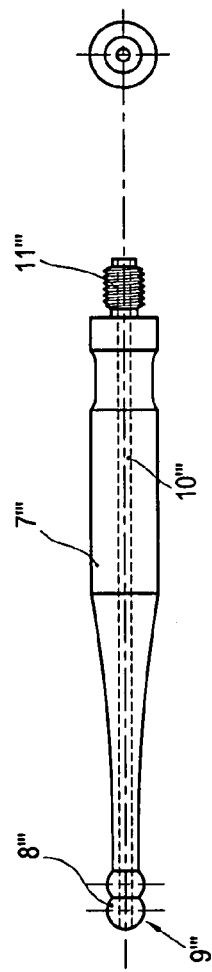
Fig.5a / Fig.5b

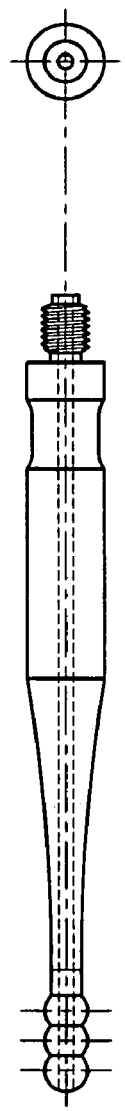
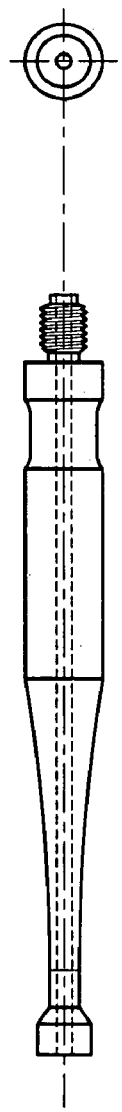
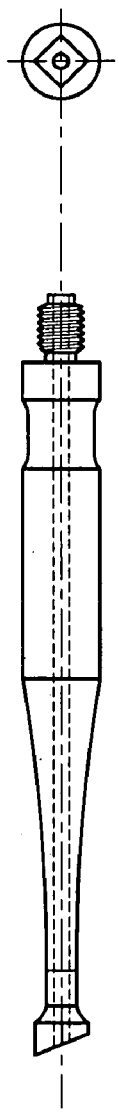
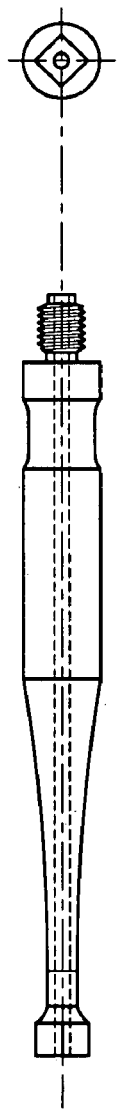
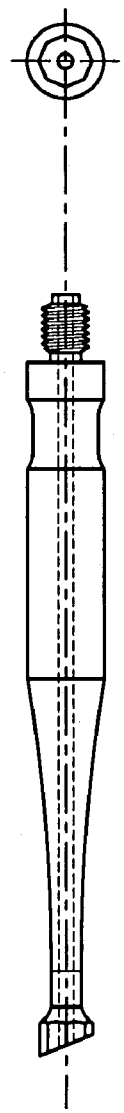
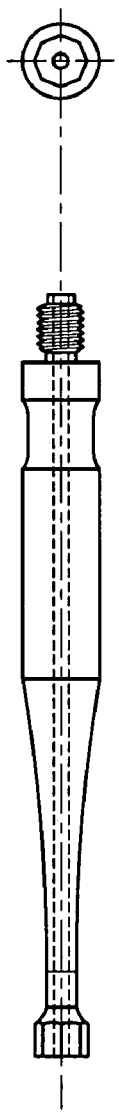
Fig.6a Fig.6b Fig.7a Fig.7b Fig.8a Fig.8b Fig.9a Fig.9b Fig.10a Fig.10b Fig.11a Fig.11b

ULTRASONIC APPARATUS FOR THE TREATMENT OF SEPTIC WOUNDS

BACKGROUND OF THE INVENTION

1. Field of the Invention

The present invention concerns an ultrasonic apparatus for the treatment of septic wounds, for example of so-called ulcerated legs or other, in particular bacterially infected wounds, which comprises a hand piece connected to an ultrasonic generator and a sonotrode attached to the hand piece.

2. Brief Description of the Background of the Invention Including Prior Art

Methods are known for a treatment of septic wounds. However, these methods are not only very painful for the patient, but in addition, very time-consuming and therefore cost intensive. A healing success is not guaranteed in connection with these conventional methods of treatment. Also a transplantation of skin parts from other locations of the body is further required in particular serious cases.

SUMMARY OF THE INVENTION

1. Purposes of the Invention

It is an object of the present invention to furnish an ultrasonic apparatus for the treatment of septic wounds, wherein the ultrasonic apparatus provides for a cost favorable method of treatment and where this method of treatment is less painful for the patient.

These and other objects and advantages of the present invention will become evident from the description which follows.

2. Brief Description of the Invention

The present invention provides a particular structure of a sonotrode of an ultrasonic apparatus. This ultrasonic treatment head or sonotrode resolves the recited problem existing and now a channel is furnished for a feeding of rock salt solution and possibly of medical healing agents such as heparin to the surface to be treated, wherein the sonotrode head can form different shapes depending on the method and kind of treatment.

In order to optimize the treatment method, the sonotrode head and the treatment face of the sonotrode have been formed in very different forms adapted to the different body forms and wound forms. The bactericidal, cleaning and massaging effect of the ultrasound are employed in the application of this so-called ultrasonic method.

The direct contact of the treatment face of the outer sonic treatment head with the pain sensitive wound regions is avoided by the employment of liquid aerosols. The microcirculation is stimulated by the application of the ultrasound, that is the infected cells are destroyed by the massaging action of the ultrasound and thus the surface of the wound is cleaned and the wound heals in a short time upon the regular application of the treatment with ultrasound.

In addition to the rock salt solution also medical healing agents such as heparin, antibiotics and the like can be applied through the channel furnished within the sonotrode, which is particularly recommended in cases of difficult accessible areas of infection. Such an ultrasonic treatment is in particular helpful in such cases, where no improvement could be achieved by injections into the area of the wound. The employment of liquids is additionally associated with the advantage that thereby the heat generated during the treatment is dissipated from the sonotrode head.

The sonotrodes are made of a wear resistant and autoclave resistant material.

As was mentioned above, the sonotrode heads or ultrasonic treatment heads of the subject of the present invention are formed very differently. The shape of the sonotrode head and of the treatment surface depend strongly on the position and shape of the wound, in order to assure an optimum employment of the ultrasonic energy. The subject of the present invention is to be explained in more detail by way of the drawings of the various embodiments.

The novel features, which are considered as characteristic for the invention are set forth in the appended claims. The invention itself, however, both as to its construction and its method of operation, together with additional objects and advantages thereof, will be best understood from the following description of specific embodiments, when read in connection with the accompanying drawing.

BRIEF DESCRIPTION OF THE DRAWING

In the accompanying drawing, in which are shown several of the various possible embodiments of the present invention:

FIG. 2a is a schematic side elevational view of a sonotrode with a treatment surface formed inclined relative to the longitudinal axis;

FIG. 2b is a schematic front elevational view onto the front face of the sonotrode according to FIG. 2a;

FIG. 3a is a schematic side elevational view of a sonotrode with a treatment face in the shape of a screwdriver blade;

FIG. 3b is a schematic front elevational view onto the front face of the sonotrode according to FIG. 3a;

FIG. 4a is a schematic side elevational view of a sonotrode with a dish shape treatment face;

FIG. 4b is a schematic front elevational view onto the front face of the sonotrode according to FIG. 4a;

FIG. 5a is a schematic side elevational view of a sonotrode with a ball shaped treatment surface;

FIG. 5b is a schematic front elevational view onto the front face of the sonotrode according to FIG. 5a;

FIG. 6a is a schematic side elevational view of a sonotrode with a three-ball shaped treatment surface;

FIG. 6b is a schematic front elevational view onto the front face of the sonotrode according to FIG. 6a;

FIG. 7a is a schematic side elevational view of a sonotrode with a round flat face treatment surface;

FIG. 7b is a schematic front elevational view onto the front face of the sonotrode according to FIG. 7a;

FIG. 8a is a schematic side elevational view of a sonotrode with a treatment surface formed inclined relative to the longitudinal axis and having a rectangular end face;

FIG. 8b is a schematic front elevational view onto the front face of the sonotrode according to FIG. 8a;

FIG. 9a is a schematic side elevational view of a sonotrode with a square flat face treatment surface;

FIG. 9b is a schematic front elevational view onto the front face of the sonotrode according to FIG. 9a;

FIG. 10a is a schematic side elevational view of a sonotrode with a treatment surface formed inclined relative to the longitudinal axis and having a round end face;

FIG. 10b is a schematic front elevational view onto the front face of the sonotrode according to FIG. 10a;

FIG. 11*a* is a schematic side elevational view of a sonotrode with a round flat face treatment surface;

FIG. 11*b* is a schematic front elevational view onto the front face of the sonotrode according to FIG. 11*a*.

DESCRIPTION OF INVENTION AND PREFERRED EMBODIMENT

Figure 1:
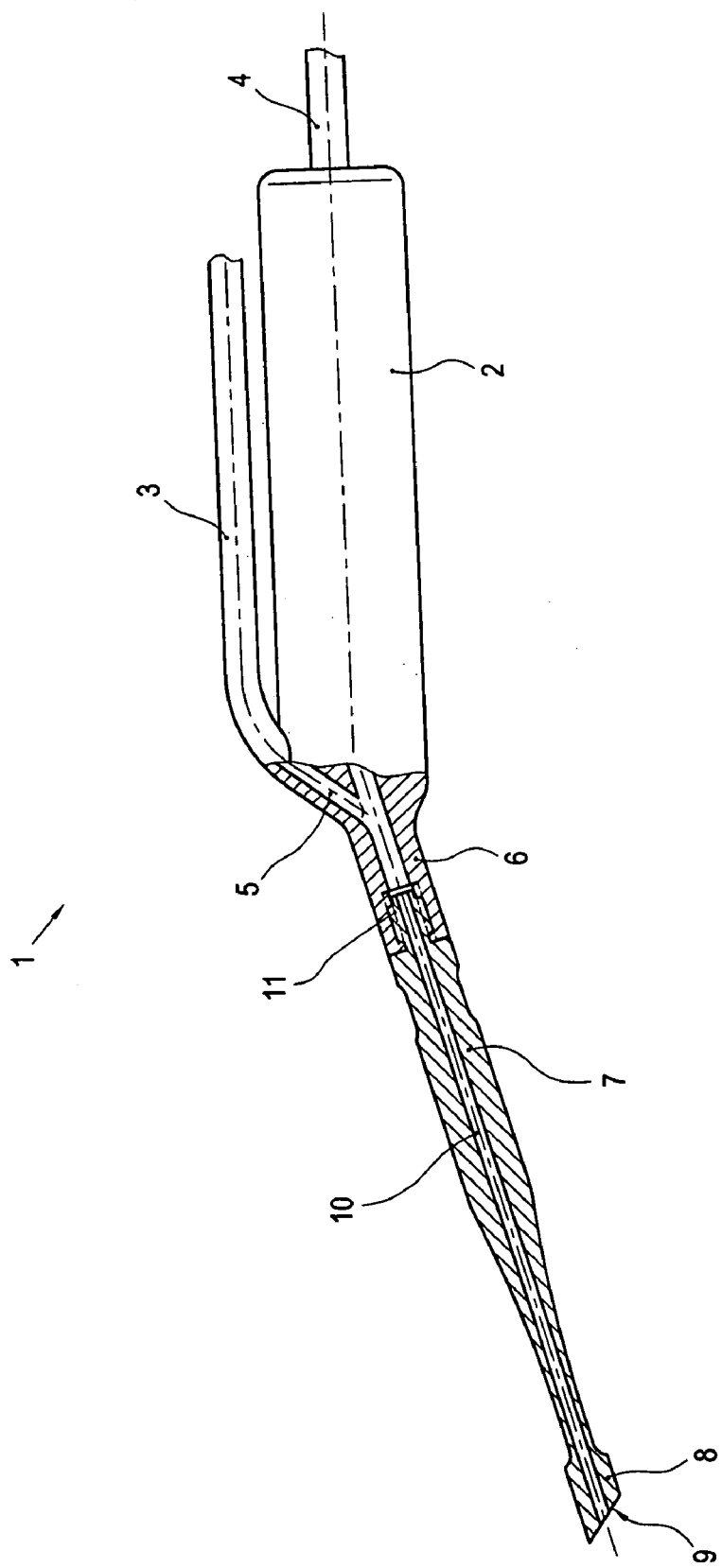
FIG. 1 is a schematic view of a side elevation and in part longitudinal section through a hand piece with an exchangeable sonotrode head.

In accordance with the present invention there is furnished an ultrasonic apparatus illustrated in FIG. 1 comprising a hand piece (1) within a handle region (2), a connection tube (3) for connecting to a supply tube, wherein rock salt solution and medical healing agents such as heparin, antibiotics and the like are fed through the feed channel (5) to the sonotrode (7) or ultrasonic treatment head. The ultrasound energy is fed to the hand piece (1) through the connection line (4) to the ultrasonic generator in a conventional way.

The hand piece (1) is equipped with a sonotrode receptacle (6), wherein the sonotrode receptacle exhibits a thread for screwing in of the sonotrode (7, 7', 7", 7'"). The respective sonotrode (7, 7', 7", 7'") is furnished with an attachment thread (11, 11', 11", 11'") corresponding to the thread of the hand piece. The liquid to be fed in to the treatment face (9, 9', 9", 9'") is led through the channel (10, 10', 10", 10'").

The sonotrode receptacle (6) can be disposed such that a sonotrode (7, 7', 7", 7'") attached to the sonotrode receptacle (6) would exhibit an angle between a longitudinal axis of the sonotrode (7, 7', 7", 7'") and an axis of the handle region (2). The angle between a longitudinal axis of the sonotrode (7, 7', 7", 7'") and an axis of the handle region (2) can be from about 5 to 25 degrees and is preferably from about 10 to 15 degrees. The total length of the handle region (2) can be from about one to two times the length of the sonotrode (7, 7', 7", 7'") and is preferably from about 1.1 to 1.4 times the length of the sonotrode (7, 7', 7", 7'").

The handle region (2) can have its axial direction aligned substantially in parallel to the axial direction of the supply tube (3). The diameter of the handle region (2) can be from about 3 to 5 times the outer diameter of the supply tube (3). The supply tube (3) can be disposed on a side opposite to the side of the sonotrode (7, 7', 7", 7'") relative to the axis of the handle region (2). A connection means can be provided at the handle region near the position of the sonotrode receptacle (6) for connecting the supply tube (3) on a side opposite to the side of the sonotrode (7, 7', 7", 7'") relative to the axis of the handle region (2). The connection means can be associated with a bore hole in the handle region (2) connecting the connection means to the feed channel (5) disposed in a middle of the sonotrode receptacle (6). The diameter of the sonotrode receptacle (6) can be from about two to four times the diameter of the channel (5).

The sonotrodes (7, 7', 7", 7'") have a sonotrode channel (10) extending in the longitudinal direction of the sonotrodes (7, 7', 7", 7'"). The diameter of the channel (5) has a diameter from about 0.5 to 4 times the diameter of the sonotrode channel (10) and are preferably of substantially the same diameter.

The ends of the sonotrodes (7, 7', 7", 7'") on the treatment side can be furnished with very different sonotrode heads (8, 8', 8", 8'"). For example, FIG. 2 shows a sonotrode head (8) with a cylindrical outer shape. The treatment face (9) is preferably milled and polished at an inclined angle relative to the longitudinal axis. The inclination angle relative to the longitudinal axis of the sonotrode can be from about 30 to 70 degrees and is preferably from about 40 to 60 degrees. It is also conceivable to furnish this face in a concave shape, in order to obtain a direct distribution of the liquid.

FIG. 3*a* shows a longitudinal view of a sonotrode (7') with an attachment thread (11'), a sonotrode channel (10') and a sonotrode head (8'), wherein the sonotrode head (8') exhibits the shape of a screwdriver blade such that the treatment faces (9') are disposed sideways as can be recognized from FIG. 3*b*. It is also conceivable in connection with this particular construction that the channel (10') is closed on the front side at the sonotrode head and that instead of the channel (10') there is provided a cross bore hole in the middle through the treatment faces (9').

The sonotrode (7") is equipped with a dish shaped sonotrode head (8") as shown in FIG. 4. This sonotrode is also connected to the hand piece (1) by way of the attachment thread (11").

The treatment liquid is fed to the treatment surface through the channel (10"). This treatment face (9") can be formed of a concave shape. The atomization power of the liquids can be further increased by such a shape of a treatment face. A dissipation of the heat generated by the ultrasound is performed simultaneously with the liquid atomization within the applicator and at the radiating border faces.

The sonotrode (7'") illustrated in FIG. 5 includes a ball shaped sonotrode head (8'"). The sonotrode (7'") can be connected to the hand piece (1) with the attachment thread (11'"). The ball shaped treatment face (9'") is supplied with the treatment liquid through the channel (10'"). Such a ball shaped formed treatment face allows a point precise application of the sonotrode (7'") in the wound region. The sonotrode head can, as shown, be comprised of two balls fitted next to each other or also as a single ball or as three or more balls. The number of the next to each other placed balls influences the intensity and the course of the ultrasound vibrations.

In addition, other formed sonotrode head shapes, such as for example spoon shape or hook shape sonotrode heads, are conceivable corresponding to special requirements in addition to the forms of the sonotrode heads illustrated in FIGS. 2 through 5. Some additional forms of sonotrode heads are shown in FIGS. 6 through 11.

For all illustrated and described forms of the sonotrode heads holds that, a dissipation of the heat generated by the ultrasound is performed simultaneously with the liquid atomization within the applicator and at the radiating border faces. Possibly required touch contacts with the wound region can be performed under low-pain based on the liquid fog present and/or based on the liquid film disposed on the surface. The bactericidal effects of the ultrasound operate sterilizing within the zone treated. While the occurrence of a liquid cavitation contributes to the cleaning of tissue zones disposed on the surface, the forced micro-massaging stimulates the microcirculation in the treatment region based on the high alternating sound pressure.

The wound cavitation processes feature a highly efficient, deep penetrating, and bactericidal effect when subjected to ultrasound assisted wound treatment in addition to mechanical rinsing effects. A special wound treatment solution according to Schikorski can be applied for this purpose. This solution is a modified local tumescence anaesthetic to which heparin has been added. Cavitations, which are defined as micro gas bubbles imploding cyclically, cause destruction of bacteria, viruses and fungi. The cavitation effects reach deeper into the wound than pure rinsing effects due to ultrasound pressure. Infected chronic wounds are characterized by an acidic wound environment that causes pain. The traits of aseptic wounds change as the bacteria remnants are broken down and the wound environment turns neutral, starting to become permanently free of pain. The neutral wound base tends to heal more quickly.

The ultrasound treatment pulse causes the wound treatment solution to penetrate deeply into the fissures of the tissue. Fibrin deposits and bacteria growth are flushed out. The central liquid supply through the sonotrode probe tip shaft has been developed for tasks where direct application to a specific area is required. The wound treatment solution also contains local anaesthetics to immediately relieve the pain. Thrombosis of the granulation capillaries is suppressed by heparinization. This also enhances the formation of new capillaries and thereby speeds up the wound healing process.

The ultrasound assisted wound treatment is associated with a number of advantages. An anaesthetising wound treatment solution contains heparin. The ultrasonic wound debridement is non-lesional. Bacteria grown and sealing fibrin layers are flushed out. The bacterial effects are highly efficient. The acidic wound environment is neutralized. An enhanced granulation is created by heparinization of the wound. Acute and long term pain are alleviated.

The frequency range of the ultrasonic sound employed can be from 20 to 80 kilo hertz.

The ultrasound assisted wound treatment provides an active treatment of chronic wounds instead of a passive care. The improvement of the wound and the alleviation of the pain are immediate upon application of the ultrasound assisted wound treatment. The wound conditioning and healing occur within a few weeks. The apparatus comprises a small mobile unit allows outpatient treatment as well as therapy in a hospital. The technology is fault tolerant and can be performed by assisting staff. The daily treatment involves extremely short times of for example from about 2 to 5 minutes depending on the size of the wound. The overall costs are maintained low by providing a single purpose apparatus.

It will be understood that each of the elements described above, or two or more together, may also find a useful application in other types of ultrasonic system configurations and wound treatment procedures differing from the types described above.

While the invention has been illustrated and described as embodied in the context of an ultrasonic apparatus for the treatment of septic wounds, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. An ultrasonic apparatus for the treatment of septic wounds comprising
   a hand piece (1) having a first connection means (4) disposed along a center axis of the hand piece (1) for connecting to an ultrasonic generator and having a second connection means disposed sideways relative to the center axis of the hand piece (1) for connecting to a liquid storage;
   a sonotrode receptacle disposed on the hand piece;
   a feed channel disposed in the hand piece, connected to the first connection means (4), connected to the second connection means, and having an open end in the sonotrode receptacle;
   a sonotrode (7) having a sonotrode head (8) and attached to the sonotrode receptacle disposed on the hand piece;
   a sonotrode channel (10, 10', 10", 10"') disposed in the sonotrode, having an open first end to match the position of the open end of the feed channel, having a single opening in a second end disposed in the sonotrode head (8), and furnished for the feeding in of treatment liquid such as rock salt solution and possibly of medical healing agents such as heparin, antibiotics and the like to the treatment face (9, 9', 9", 9"') of the sonotrode head (8, 8', 8", 8"') adapted to a required treatment mode through the single opening.

2. The ultrasonic apparatus for the treatment of septic wounds according to claim 1 wherein the sonotrode head (8) comprises a cylindrical shape part, wherein the treatment face (9) is disposed at an inclined angle relative to the longitudinal axis of the sonotrode.

3. An ultrasonic apparatus for the treatment of septic wounds
   comprising
   a hand piece (1) having a first connection means (4) disposed on a center axis of the hand piece (1) for connecting to an ultrasonic generator and having a second connection means disposed sideways relative to the center axis of the handpiece (1) for connecting to a liquid storage;
   a sonotrode receptacle disposed on the hand piece;
   a feed channel disposed in the hand piece and having an open end in the sonotrode receptacle;
   a sonotrode (7) having a sonotrode head (8) and attached to the sonotrode receptacle disposed on the hand piece;
   a sonotrode channel (10, 10', 10", 10"') disposed in the sonotrode, having an open first end to match the position of the open end of the feed channel, having a single opening in a second end disposed in the sonotode head (8), and furnished for the feeding in of treatment liquid such as rock salt solution and possibly of medical healing agents such as heparin, antibiotics and the like to the treatment face (9, 9', 9", 9"') of the sonotrode head (8, 8', 8", 8"') adapted to a required treatment mode,
   wherein the treatment face (9) has a concave shape.

4. The ultrasonic apparatus for the treatment of septic wounds according to claim 1 wherein the sonotrode head (8') is formed in the shape of a screwdriver blade furnished with parallel side faces.

5. The ultrasonic apparatus for the treatment of septic wounds according to claim 1 wherein the sonotrode head (8") is formed in dish shape.

6. An ultrasonic apparatus for the treatment of septic wounds
   comprising
   a hand piece (1) having a first connection means (4) disposed on a center axis of the handpiece (1) for connecting to an ultrasonic generator and having a second connection means disposed sideways relative to the center axis of the hand piece (1) for connecting to a liquid storage;
   a sonotrode receptacle disposed on the hand piece;
   a feed channel disposed in the hand piece and having an open end in the sonotrode receptacle;
   a sonotrode (7) having a sonotrode head (8) and attached to the sonotrode receptacle disposed on the hand piece;

a sonotrode channel (10, 10', 10", 10''') disposed in the sonotrode, having an open first end to match the position of the open end of the feed channel, having a single opening in a second end in the sonotrode head (8), and furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to a required treatment mode through the single opening, wherein a treatment face (9") of the sonotrode head (8") is formed with a concave dish shape.

7. An ultrasonic apparatus for the treatment of septic wounds
comprising
a hand piece (1) having a first connection means (4) disposed on a center axis of the handle (1) for connecting to an ultrasonic generator and having a second connection means disposed sideways relative to the center axis of the handle (1) for connecting to a liquid storage;
a sonotrode receptacle disposed on the hand piece;
a feed channel disposed in the hand piece and having an open end in the sonotrode receptacle;
a sonotrode (7) having a sonotrode head (8) and attached to the sonotrode receptacle disposed on the hand piece;
a sonotrode channel (10, 10', 10", 10''') disposed in the sonotrode, having an open first end to match the position of the open end of the feed channel, having a single opening in a second end in the sonotrode head (8), and furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to a required treatment mode through the single opening,
wherein the sonotrode head (8''') and therewith also a treatment surface (9''') are formed with a ball shape.

8. An ultrasonic apparatus for the treatment of septic wounds
comprising
a hand piece (1) having a first connection means (4) disposed centered relative to a center axis of the hand piece (1) for connecting to an ultrasonic generator and having a second connection means disposed sideways relative to the center axis of the hand piece (1) for connecting to a liquid storage;
a sonotrode receptacle disposed on the hand piece;
a feed channel disposed in the hand piece and having an open end in the sonotrode receptacle;
a sonotrode (7) having a sonotrode head (8) and attached to the sonotrode receptacle disposed on the hand piece;
a sonotrode channel (10, 10', 10", 10''') disposed in the sonotrode, having an open first end to match the position of the open end of the feed channel, having a single opening in a second end in the sonotrode head (8), and furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to a required treatment mode through the single opening,
wherein the sonotrode head comprises two balls set next to each other.

9. The ultrasonic apparatus for the treatment of septic wounds according to claim 1 wherein treatment faces (9, 9', 9", 9''') of the sonotrode (8, 8', 8", 8''') are polished and wherein the sonotrode (7) as seen from a thread of the sonotrode (7) narrows down in the middle of the sonotrode (7) and has a thicked end section with the sonotrode head (8) with the treatment face (9).

10. The ultrasonic apparatus for the treatment of septic wounds according to claim 1 wherein the sonotrodes (7, 7', 7", 7''') are made of a wear resistant and autoclave resistant material.

11. An ultrasonic apparatus for the treatment of septic wounds, which comprises a hand piece (1) having a tube disposed on a center axis of the hand piece (1) connected to an ultrasonic generator and having a second tube disposed away from the center axis connected to liquid storage and a sonotrode (7) attached to the hand piece (1), wherein a channel (10, 10', 10", 10'''), is furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to the required treatment mode through a single opening disposed in the treatment face (9, 9', 9", 9''').

12. The ultrasonic apparatus for the treatment of septic wounds according to claim 11 wherein the sonotrode head (8) comprises a cylindrical shape part, wherein the treatment face (9) is disposed at an inclined angle relative to the longitudinal axis of the sonotrode.

13. An ultrasonic apparatus for the treatment of septic wounds,
which comprises a hand piece (1) having a tube disposed on a center axis of the hand piece (1) connected to an ultrasonic generator, and having a second tube disposed away from the center axis connected to liquid storage and a sonotrode (7) attached to the hand piece (1), wherein a channel (10, 10', 10", 10''') is furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to the required treatment mode through a single opening disposed in the treatment face (9, 9, 9, 9'''),
wherein the treatment face (9) has a concave shape.

14. The ultrasonic apparatus for the treatment of septic wounds according to claim 11 wherein the sonotrode head (8') is formed in the shape of a screwdriver blade furnished with parallel side faces.

15. The ultrasonic apparatus for the treatment of septic wounds according to claim 11 wherein the sonotrode head (8") is formed in dish shape.

16. An ultrasonic apparatus for the treatment of septic wounds,
which comprises a hand piece (1) having a tube disposed on a center axis of the hand piece (1) connected to an ultrasonic generator and having a second tube disposed away from the center axis connected to liquid storage and a sonotrode (7) attached to the hand piece (1), wherein a channel (10, 10', 10", 10''') is furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to the required treatment mode through a single opening disposed in the treatment face (9, 9', 9', 9'''),
wherein the treatment face (9") of the sonotrode head (8") is formed with a concave dish shape.

17. An ultrasonic apparatus for the treatment of septic wounds, which comprises a hand piece (1) having a tube disposed on a center axis of the hand piece (1) connected to an ultrasonic generator and having a second tube disposed away from the center axis connected to liquid storage and a sonotrode (7) attached to the hand piece (1), wherein a channel (10, 10', 10", 10''') is furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to the required treatment mode through a single opening disposed in the treatment face (9, 9, 9", 9'''), wherein the sonotrode head (8''') and therewith also the treatment surface (9''') are formed with a ball shape.

18. The ultrasonic apparatus for the treatment of septic wounds according to claim 17 wherein the sonotrode head comprises one or several balls set next to each other.

19. The ultrasonic apparatus for the treatment of septic wounds according to claim 11 wherein the treatment faces (9, 9', 9", 9''') of the sonotrode head (8, 8', 8", 8''') are polished.

20. The ultrasonic apparatus for the treatment of septic wounds according to claim 11 wherein the sonotrodes (7, 7', 7", 7''') are made of a wear resistant and autoclave resistant material.

21. A method for the treatment of septic wounds comprising
- connecting a hand piece having a sonotrode receptacle and having a first connection means disposed on a center axis of the hand piece to an ultrasonic generator, wherein a feed channel is disposed in the hand piece, connected to the first connection means, and having an open end in the sonotrode receptacle;
- connecting the hand piece having a second connection means disposed sideways relative to the center axis of the hand piece to a liquid storage, wherein the second connection means is connected to the feed channel;
- attaching a sonotrode having a sonotrode head to the sonotrode receptacle disposed on the hand piece;
- exposing a surface of a wound;
- delivering a liquid atomized by ultrasound to the wound through a sonotrode channel disposed in the sonotrode and having a single output opening in the sonotrode head, said sonotrode channel having an open first end to match the position of the open end of the feed channel, and furnished for the feeding in of a treatment liquid such as rock salt solution and possibly of medical healing agents such as heparin, antibiotics and the like to the treatment face of the sonotrode head adapted to the exposed wound.

22. An ultrasonic apparatus for the treatment of septic wounds comprising
- a hand piece (1) having a first connection means disposed on a center axis of the hand piece (1) for connecting to an ultrasonic generator and having a second connection means disposed sideways relative to the center axis of the hand piece (1) for connecting to a liquid storage;
- a sonotrode receptacle disposed on the hand piece;
- a feed channel disposed in the hand piece and having an open end in the sonotrode receptacle;
- a sonotrode (7) having a sonotrode head (8) and attached to the sonotrode receptacle disposed on the hand piece;
- a sonotrode channel (10, 10', 10", 10''') disposed in the sonotrode, having an open first end to match the position of the open end of the feed channel, having a single opening in a second end in the sonotrode head (8), and furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to a required treatment mode and wherein the ultrasonic apparatus does not include a laser beam.

23. An ultrasonic apparatus for the treatment of septic wounds comprising
- a hand piece (1) having a first connection means disposed on a center axis of the hand piece (1) for connecting to an ultrasonic generator and having a second connection means disposed sideways relative to the center axis of the hand piece (1) for connecting to a liquid storage;
- a sonotrode receptacle disposed on the hand piece;
- a feed channel disposed in the hand piece and having an open end in the sonotrode receptacle;
- a sonotrode (7) having a sonotrode head (8) and attached to the sonotrode receptacle disposed on the hand piece;
- a sonotrode channel (10, 10', 10", 10''') disposed in the sonotrode, having an open first end to match the position of the open end of the feed channel, having a single opening in a second end in the sonotrode head (8), and furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to a required treatment mode and having a single outlet port coming out from a second end of the sonotrode.

24. An ultrasonic apparatus for the treatment of septic wounds comprising
- a hand piece (1) having a first connection means disposed on a center axis of the hand piece (1) for connecting to an ultrasonic generator and having a second connection means disposed away from the center axis of the hand piece (1) for connecting to a liquid storage;
- a sonotrode receptacle disposed on the hand piece;
- a feed channel disposed in the hand piece and having an open end in the sonotrode receptacle;
- a sonotrode (7) having a sonotrode head (8) and attached to the sonotrode receptacle disposed on the hand piece;
- a sonotrode channel (10, 10', 10", 10''') disposed in the sonotrode, having an open first end to match the position of the open end of the feed channel, having a single opening in a second end in the sonotrode head (8), and furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to a required treatment mode and wherein no envelope surrounds the sonotrode.

25. An ultrasonic hand piece for the treatment of septic wounds comprising
- a handle region having an axial direction and with a connection line disposed in a center of and running through the handle region for feeding ultrasonic energy to the ultrasonic hand piece;
- a sonotrode receptacle, wherein the sonotrode receptacle exhibits a thread;
- a sonotrode with a sonotrode head, wherein the sonotrode is furnished with an attachment thread corresponding to the thread of the sonotrode receptacle, and wherein the sonotrode receptacle is disposable such that the sonotrode attached to the sonotrode receptacle exhibits an angle larger than 5 degrees between a longitudinal axis of the sonotrode and the center axis of the handle region;

a bore hole disposed in the handle region near the position of the sonotrode receptacle for connecting to a supply tube, wherein the handle region has the axial direction aligned substantially in parallel to an axial direction of the supply tube;

a feed channel disposed in a middle of the sonotrode receptacle;

a sonotrode channel disposed in a middle of the sonotrode, wherein the sonotrode channel is connected to the feed channel and has a single output opening in the sonotrode head.

26. The ultrasonic handle piece for the treatment of septic wounds according to claim 25, wherein an angle between the longitudinal axis of the sonotrode and the axis of the handle region is from about 5 to 25 degrees.

27. The ultrasonic handle piece for the treatment of septic wounds according to claim 25, wherein a diameter of the handle region is from about 3 to 5 times an outer diameter of the supply tube, wherein the supply tube is disposed on a side opposite to the side of the sonotrode relative to the axial direction of the handle region.

28. The ultrasonic handle piece for the treatment of septic wounds according to claim 25, wherein the feed channel has a diameter of from about 0.5 to 4 times a diameter of the sonotrode channel.

29. The ultrasonic hand piece for the treatment of septic wounds according to claim 25, wherein a total length of the handle region is from about one to two times a length of the sonotrode.

30. The ultrasonic hand piece for the treatment of septic wounds according to claim 25, wherein the sonotrode head has a treatment face, and wherein the treatment face is inclined and polished.

31. The ultrasonic hand piece for the treatment of septic wounds according to claim 30, wherein an inclination angle of the treatment face relative to the longitudinal axis of the sonotrode is from about 30 to 70 degrees.

32. The ultrasonic handle piece for the treatment of septic wounds according to claim 25, wherein a treatment liquid is fed to a treatment surface through the sonotrode channel from the supply tube, and wherein the flow of the treatment liquid is controlled by the ultrasound energy being fed to the handle region.

33. An ultrasonic apparatus for the treatment of septic wounds comprising a hand piece (1) having a first connection means (4) disposed on a center axis of the hand piece (1) for connecting to an ultrasonic generator and having a second connection means disposed away from the center axis of the hand piece (1) for connecting to a liquid storage;

a sonotrode receptacle disposed on the hand piece;

a feed channel disposed in the hand piece and having an open end in the sonotrode receptacle, wherein a longitudinal axis of the feed channel forms an angle of more than 5 degrees with a longitudinal axis of the first connection means and with a longitudinal axis of the second connection means; a sonotrode (7) having a sonotrode head (8) and attached to the sonotrode receptacle disposed on the hand piece;

a sonotrode channel (10, 10', 10", 10''') disposed in the sonotrode, having an open first end to match the position of the open end of the feed channel, having a single opening in a second end in the sonotrode head (8), and furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to a required treatment mode through the single opening.

34. A method for the treatment of septic wounds comprising connecting a hand piece having a sonotrode receptacle and having a first connection means disposed on a center axis of the hand piece to an ultrasonic generator, wherein a feed channel is disposed in the hand piece having an open end in the sonotrode receptacle;

connecting the hand piece having a second connection means disposed away from the center axis of the hand piece to a liquid storage;

attaching a sonotrode having a sonotrode head to the sonotrode receptacle disposed on the hand piece, wherein the sonotrode is positioned inclined relative to the ultrasonic generator and to liquid storage;

exposing a surface of a wound;

delivering a liquid atomized by ultrasound to the wound through a sonotrode channel disposed in the sonotrode, said sonotrode channel having an open first end to match the position of the open end of the feed channel, having a single opening in a second end in the sonotrode head, and furnished for the feeding in of a treatment liquid such as rock salt solution and possibly of medical healing agents such as heparin, antibiotics and the like to the treatment face of the sonotrode head adapted to the exposed wound.

35. An ultrasonic apparatus for the treatment of septic wounds comprising a hand piece (1) having a first connection means disposed on a center axis of the hand piece (1) for connecting to an ultrasonic generator and having a second connection means disposed sideways relative to the center axis of the hand piece (1) for connecting to a liquid storage;

a sonotrode receptacle disposed on the hand piece;

a feed channel disposed in the hand piece and having an open end in the sonotrode receptacle, wherein a longitudinal axis of the feed channel forms an angle of more than 5 degrees with a longitudinal axis of the first connection means and with a longitudinal axis of the second connection means;

a sonotrode (7) having a sonotrode head (8) and attached to the sonotrode receptacle disposed on the hand piece;

a sonotrode channel (10, 10', 10", 10''') disposed in the sonotrode, having an open first end to match the position of the open end of the feed channel, having a single output opening in a second end in the sonotrode head (8), and furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to a required treatment mode through the single output opening and wherein no envelope surrounds the sonotrode.

36. An ultrasonic apparatus for the treatment of septic wounds comprising a first connection means (4) for connecting to an ultrasonic generator;

a second connection means for connecting to a liquid storage;

a feed channel connected to the first connection means (4), connected to the second connection means, and having an open end;

a sonotrode receptacle receiving the open end;
a handpiece defining the first connection means, the second connection means, the feed channel, and the sonotrode receptacle wherein the first connection means is disposed on a center axis of the hand piece and wherein the second connection piece is disposed sideways relative to the center axis of the hand piece;
a sonotrode (7) having a sonotrode head (8) and attached to the sonotrode receptacle disposed on the hand piece;
a sonotrode channel (10, 10', 10", 10''') disposed in the sonotrode, having an open first end to match the position of the open end of the feed channel, having a single output opening in a second end in the sonotrode head (8), and furnished for the feeding in of treatment liquid such as rock salt solution and possibly of medical healing agents such as heparin, antibiotics and the like to the treatment face (9, 9', 9", 9''') of the sonotrode head (8, 8', 8", 8''') adapted to a required treatment mode through the single output opening.

* * * * *